United States Patent [19]

Litterer et al.

[11] Patent Number: 4,937,395

[45] Date of Patent: Jun. 26, 1990

[54] PROCESS FOR THE PREPARATION OF FLUOROBENZENES

[75] Inventors: Heinz Litterer, Bad Schwalbach; Hans J. Metz, Darmstadt; Theodor Papenfuhs, Frankfurt am Main; Frank P. Sistig, Hofheim am Taunus; Ernst I. Leupold, Neu-Anspach, all of Fed. Rep. of Germany

[73] Assignee: Hoechst Aktiengesellschaft, Frankfurt, Fed. Rep. of Germany

[21] Appl. No.: 379,827

[22] Filed: Jul. 14, 1989

[30] Foreign Application Priority Data

Jul. 16, 1988 [DE] Fed. Rep. of Germany ....... 3824141

[51] Int. Cl.$^5$ ..................... C07C 17/24; C07C 17/33; C07C 25/13
[52] U.S. Cl. ..................... 570/142; 570/127
[58] Field of Search .......................... 570/142

[56] References Cited

U.S. PATENT DOCUMENTS

| | | | |
|---|---|---|---|
| 2,647,933 | 8/1953 | La Zente et al. | 570/142 |
| 2,967,894 | 1/1961 | Pummer et al. | 570/142 |
| 3,020,321 | 2/1962 | Gibbs | 570/142 |
| 3,501,541 | 3/1970 | Dubeck et al. | 570/142 |
| 4,075,252 | 2/1978 | Boudakian | 260/649 F |
| 4,096,196 | 6/1978 | Boudakian | 260/650 F |
| 4,668,832 | 5/1987 | Kruper | 570/142 |
| 4,847,442 | 7/1989 | Nolawajek et al. | 570/142 |

FOREIGN PATENT DOCUMENTS

| | | | |
|---|---|---|---|
| 740935 | 11/1955 | United Kingdom | 570/142 |
| 874867 | 8/1961 | United Kingdom | 570/142 |

OTHER PUBLICATIONS

G. Schiemann et al., Berichte d. D. Chem. Gesellschaft 62:3035-3043 (1929) (In German).
D. T. Flood, Organic Syntheses, Coll. 2:295-298 (1943).
K. G. Rutherford et al., J. Org. Chem. 26:5149-5152 (1961).

Primary Examiner—J. E. Evans

[57] ABSTRACT

A process for the preparation of fluorobenzenes of the formula I

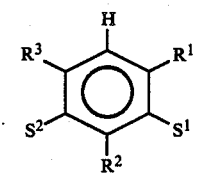

wherein $R^1$, $R^2$ and $R^3$ are equal or different and represent H, F, Cl or alkyl having from 1 to 3 carbon atoms, at least one of these radicals being fluorine, and $S^1$ and $S^2$ being equal or different and represent H or a group reducing the electron density at the benzene nucleus, which comprises subjecting a compound of the formula II

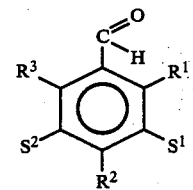

in which $R^1$, $R^2$, $R^3$, $S^1$ and $S^2$ have the aforementioned meaning to a decarbonylation at a zeolite catalyst.

20 Claims, No Drawings

PROCESS FOR THE PREPARATION OF FLUOROBENZENES

DESCRIPTION

The present invention relates to a process for the preparation of substituted or unsubstituted fluorobenzenes by catalytic decarbonylation of the corresponding fluorobenzaldehydes.

According to the state of the art, fluoroaromatics have been prepared according to the Balz-Schiemann method (D. T. Flood, Org. Synth. Coll. II, 295 (1943)) by diazotization of aniline derivatives which contain halogen, in particular fluorine, and, if appropriate, $NH_2$ or $NO_2$ on the nucleus. Thus, for example, 1,3-difluorobenzene has been obtained by successive diazotization of m-phenylenediamine in anhydrous hydrogen fluoride in 31% yield (G. Schiemann et al., Ber. 62, 3039 (1929)). As an alternative synthesis, the diazotization of m-fluoroaniline in the presence of ammonium bifluoride, tertiary amines and dimethyl sulfoxide has been described. The yields are between 46 and 73% (U.S. Pat. Nos. 4,075,252 and 4,096,196).

Similarly low yields (27–40%) are obtained in the preparation of 1,4-difluorobenzene from p-phenylenediamine according to Balz-Schiemann (G. Schiemann et al., Ber. 62, 3039 (1929)). Even the addition of tertiary amines, in order to obtain more favorable decomposition temperatures, or the use of aryldiazonium hexafluorophosphate ($ArN_2PF_6$) (K. G. Rutherford et al., J. Org. Chem. 26, 5149 (1961)) does not in general provide less expensive access to halogen-substituted fluorobenzenes.

It was therefore the object to develop a process in which a specific reaction procedure and also the other disadvantages usual in this case, such as the handling of hydrogen fluoride or expensive auxiliary chemicals, are avoided. The invention follows a completely different approach for this purpose.

The present invention relates to a process in which, by catalytic decarbonylation of fluorobenzaldehydes of the formula II (see Patent claim 1), in which $R^1$, $R^2$ and $R^3$ independently of one another represent H, F, Cl and/or alkyl having 1 to 3 carbon atoms, but at least one of these radicals is fluorine and preferably at least one of the radicals $R^1$ and $R^3$ is hydrogen, and $S^1$ and $S^2$ independently of one another are H and/or radicals which reduce the electron density on the benzene nucleus, preferably H, the corresponding fluorobenzenes of the formula I (see Patent claim 1) are obtained in very good yield on zeolite catalysts, preferably in the presence of hydrogen.

The zeolites used in the process according to the invention are above all natural or synthetic crystalline alumosilicates. The basic building blocks of these zeolites are $SiO_4^-$- and $AlO_4^-$- tetrahedra which are linked via oxygen atoms as bridges and therefore have regular structures with cavities and pore orifices. However, other zeolites are also suitable in which a part of the aluminum or silicon is replaced by other lattice atoms, preferably boron, iron, gallium, germanium, titanium and/or zirconium. The negative charges of the $AlO_4^-$-tetrahedra are, as a result of the synthesis, partially compensated by cations such as $H^+$, $Na^+$, $K^+$, $Ca^{2+}$, $Mg^{2+}$ or organic cations such as $N^+R_4$ and $P^+R_4$.

Those catalysts are also suitable for the process according to the invention in which the cations introduced by the synthesis have been exchanged by conventional methods for other cations, so that products with widely different properties are present (D. W. Breek: Zeolite Molecular Sieves, 1974*) The use of catalysts is also possible which have been modified by a thermal treatment of those zeolite types which contain organic cations such as $N^+R_4$ or $P^+R_4$.

*Chapter 7, pp. 540-552 and 569-571.

Those zeolites are preferably used, however, which have been modified by ion exchange with monovalent, divalent and/or trivalent cations, advantageously with $NH_4^+$, $H^+$, $Be^{2+}$, $Mg^{2+}$, $Ca^{2+}$, $La^{3+}$ or cations of the rare earths or with combinations of these elements, and have thus been converted into a catalytically active form, those with $NH_4^+$ and $H^+$ being very particularly preferred.

Examples of zeolites suitable for the process according to the invention—known to those skilled in the art as adsorbants or as catalysts for hydrocarbon conversions—are the zeolites ZSM-5 (U.S. Pat. No. 3,702,886), ZSM-8 (British Patent No. 1,334,243), ZSM-11 (U.S. Pat. No. 3,709,979), ZSM-12 (U.S. Pat. No. 3,832,449), ZSM-20 (U.S. Pat. No. 3,972,983), ZSM-21 (U.S. Pat. No. 4,046,859), ZSM-23 (U.S. Pat. No. 4,076,842) and ZSM-48 (European Published Application No. 0,034,918) or mordenite. All of these catalysts can be employed as such, but are preferably used in the H form.

The zeolites of the pentasil type are particularly suitable for the present process, the term pentasils being based on the definition by Kokotailo and Meier ("Pentasil family of high silicon crystalline materials" in Special Publication No. 33 of the Chemical Society, London 1980). The Si/Al ratio of these zeolites is in general between 5 and 4,000, preferably between 10 and 2,000.

The aluminum content of the zeolites used according to the invention can, for the purpose of more extensive modification, be reduced within the limits mentioned by treatment with mineral acids, organic acids or chelating substances.

Zeolites having a faujasite structure and those based on aluminum phosphate or aluminum silicophosphate can also be employed in the process according to the invention.

For the use according to the invention, the zeolites are converted into a suitable application form, for example an extruded form, advantageously with the aid of binders. Suitable binders are above all oxides, hydroxides or hydroxychlorides of aluminum and the oxides of silicon, titanium and zirconium, as well as clay minerals.

The preferably used zeolite catalysts are activated in the usual manner by calcination, which represents a further type of modification. Occasionally, it is advantageous to repeat the ion exchange and calcination several times. The calcination is preferably carried out at 350°–700° C. In order to improve the stabilization, it is sometimes advantageous to carry out the calcination in the presence of steam, ammonia or mixtures thereof at temperatures of at least 600° C. and then, if desired, to raise the temperature up to 900° C.

The decarbonylation can be carried out either in the gas phase or in the liquid phase, operation in the gas phase being preferred. In the case of gas phase operation, the reaction temperatures are in general 250°–600° C., preferably 300°–500° C. Preferably, the process is carried out at atmospheric pressure or at the back pressure resulting from the passage of the gaseous starting materials through the catalyst which is, for example, arranged in a fixed bed. The pressures are, for example, from atmospheric pressure up to 20 bar, preferably up to 5 bar.

Advantageously, hydrogen and/or substances which are inert towards the reactants under the reaction conditions applied, such as vaporized aliphatic hydrocarbons such as pentane fractions, hexane fractions or heptane fractions, or gases such as nitrogen or carbon dioxide, are passed over the catalyst in addition to the aldehydes which are to be decarbonylated.

The loading (weight unit of the starting material per hour per weight unit of catalyst—dimension $h^{-1}$ = WHSV = weight hourly space velocity) is preferably between 0.1 and 10 $h^{-1}$.

As can be seen from the examples which follow, a regeneration of the catalyst is necessary after some time. This can be carried out by controlled burning-off with an oxygen-containing gas.

EXAMPLES (1) A ZSM-5 zeolite (pentasil structure) synthesized with 0.2% by weight of aluminum according to U.S. Pat. No. 3,702,886 was, after thermal pretreatment for 14 hours, mixed with alumina in the ratio of 2:1, pasted with 10% by weight of a 2% strength by weight nitric acid and processed to give 1.4 mm thick extrudates. The catalyst extrudates obtained were then dried for 1 hour at 120° C. and then calcined for 2 hours at 600° C. The extracts were then contacted repeatedly with a 10% strength ammonium sulfate solution and the sodium ions present from the synthesis were thus exhaustively exchanged for $NH_4^+$. The hydrogen form of ZSM-5 zeolite was obtained by another thermal treatment of these extrudates at 600° C.

A fixed-bed reactor of 20 mm internal diameter and 600 mm length was charged with 100 ml of the catalyst and fed with 60 ml of 2,4-difluorobenzaldehyde at atmospheric pressure and 400° C. To reduce the inlet partial pressure, 80 l of hydrogen per hour were additionally fed in. The results of the experiment are summarized in Table 1. The 1,3-difluorobenzene boiling at 83° C. was isolated by simple distillation.

TABLE 1

Preparation of 1,3-difluorobenzene by decarbonylation of 2,4-difluorobenzaldehyde-

| Temperature (°C.) | Composition of the reactor product (% by weight) | | after hours (h) |
|---|---|---|---|
| | 1,3-difluoro-benzene | 2,4-difluoro-benzaldehyde | |
| 400 | 99.0 | 1.0 | 1 |
| 400 | 99.0 | 1.0 | 3 |
| 400 | 98.0 | 2.0 | 7 |
| 400 | 94.0 | 6.0 | 12 |
| 400 | 81.0 | 19.0 | 18 |

(2) Example 1 was repeated using an H-ZSM-11 catalyst (pentasil structure). The results do not differ from those obtained with the H-ZSM-5 catalyst.

(3) When 2-chloro-6-fluorobenzaldehyde was employed in place of the 2,4-difluorobenzaldehyde used in Example 1 and the procedure of Example 1 was followed in other respects, the following values were obtained over an experimental cycle lasting several hours:

TABLE 2

Preparation of 3-chloro-fluorobenzene

| Temperature (°C.) | Content of the reactor product (% by weight) | | after hours (h) |
|---|---|---|---|
| | 3-chloro-fluoro-benzene | 2-chloro-6-fluoro benzaldehyde | |
| 420 | 33.2 | 64.9 | 1 |
| 420 | 30.2 | 69.1 | 3 |
| 420 | 24.6 | 74.9 | 8 |
| 420 | 22.9 | 76.7 | 12 |
| 420 | 21.7 | 77.6 | 20 |

(4) Conversion of 2,4-difluorobenzaldehyde on an H-ZSM-12 catalyst

When Examples 1 to 3 are modified in such a way that, in place of a zeolite of the ZSM-5 or ZSM-11 series, the H form of ZSM-12 zeolite was used and the fixed-bed reactor was operated at atmospheric pressure with a loading of 0.6 $h^{-1}$ at 370° C. with the addition of 60 liters of hydrogen per hour, 73% of the 2,4-difluorobenzaldehyde sent in were converted on this catalyst. Selectivity to 1,3-difluorobenzene was 98%.

(5) A ZSM-48 zeolite described in Example 3 of European Published Application No. 0,034,918 was synthesized and converted into the H form by known methods.

The experimental apparatus described in Example 1 was charged with 50 ml of H-ZSM-48 catalyst. After feeding in 60 l of hydrogen per hour at atmospheric pressure, the reaction temperature was set to 450° C. in the course of 30 minutes and 4-chloro-2-fluorobenzaldehyde was then fed in at a loading of 1.2 $h^{-1}$.

A conversion of 87% was calculated from the analytical data of the products collected in the first 6 hours of operation. The selectivity to 3-chloro-fluorobenzene was 90%.

We claim:

1. A process for the preparation of fluorobenzenes of the formula I

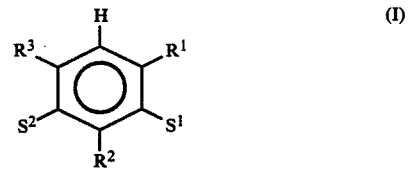

(I)

wherein $R^1$, $R^2$ and $R^3$ are equal or different and represent H, F, Cl or alkyl having from 1 to 3 carbon atoms, at least one of these radicals being fluorine, and $S^1$ and $S^2$ being equal or different and represent H or a group reducing the electron density at the benzene nucleus, which comprises subjecting a compound of the formula II

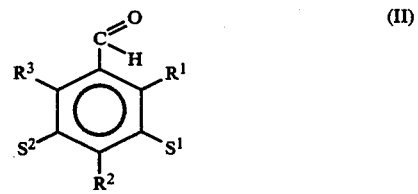

(II)

in which $R^1$, $R^2$, $R^3$, $S^1$ and $S^2$ have the aforementioned meaning to a decarbonylation at a zeolite catalyst.

2. A process as claimed in claim 1, wherein at least one of the radicals $R^1$ and $R^3$ represents hydrogen.

3. A process as claimed in claim 1, wherein $S^1$ and $S^2$ represent hydrogen.

4. A process as claimed in claim 1, wherein the decarbonylation is carried out in the presence of hydrogen or a compound which is inert towards the reactants under the reaction conditions applied, or both.

5. A process as claimed in claim 4, wherein the said inert compound is a fraction of pentanes, hexanes, or heptanes, nitrogen, carbon dioxide or a combination thereof.

6. A process as claimed in claim 1, wherein the zeolite is an alumosilicate in which a part of the aluminum or silicon may be replaced by other atoms in the lattice.

7. A process as claimed in claim 6, wherein the said other element is boron, iron, gallium, germanium, titanium, zirconium or a combination thereof.

8. A process as claimed in claim 6, wherein the ratio between Si and Al in the zeolite is in the range of from 5 to 4000.

9. A process as claimed in claim 8, wherein the ratio between Si and Al in the zeolite is in the range of from 10 to 2000.

10. A process as claimed in claim 1, wherein the zeolite has a pentasil or faujasit structure or comprises aluminum phosphate or aluminum silicon phosphate.

11. A process as claimed in claim 1, wherein the zeolite used is of the type ZSM-5, ZSM-8, ZSM-11, ZSM-12, ZSM-20, ZSM-21, ZSM-23, ZSM-48, each in the ordinary or acid form, or mordenite.

12. A process as claimed in claim 1, wherein the zeolite also contains ions selected from the group consisting of $Be^{2+}$, $Mg^{2+}$, $Ca^{2+}$, $La^{3+}$, any further rare earth metal, hydrogen, ammonium and a combination of these cations.

13. A process as claimed in claim 1, wherein the zeolite used is a natural or synthetic crystalline alumosilicate.

14. A process as claimed in claim 1, which is carried out in the gaseous phase.

15. A process as claimed in claim 14, which is carried out at a temperature in the range of from 250° to 600° C.

16. A process as claimed in claim 15, which is carried out at a temperature in the range of from 300° to 500° C.

17. A process as claimed in claim 14, which is carried out at a pressure in the range of from atmospheric pressure to 20 bar.

18. A process as claimed in claim 14, which is carried out at a pressure in the range of from atmospheric pressure to 5 bar.

19. A process as claimed in claim 18, which is carried out at atmospheric pressure or the dynamic pressure resulting on feeding of the gaseous starting materials through the catalytic system.

20. A process as claimed in claim 14, which is carried out at a temperature in the range of from 250° to 600° C. and at a pressure in the range of from atmospheric pressure to 20 bar.

* * * * *